(12) United States Patent
Marsh et al.

(10) Patent No.: US 9,364,668 B2
(45) Date of Patent: *Jun. 14, 2016

(54) APPARATUS, SYSTEMS, AND METHODS FOR TREATING BODY ORGAN AGING

(71) Applicant: Ohio State Innovation Foundation, Columbus, OH (US)

(72) Inventors: Clay B. Marsh, Columbus, OH (US); Ali R. Rezai, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/839,079

(22) Filed: Aug. 28, 2015

(65) Prior Publication Data

US 2015/0367128 A1    Dec. 24, 2015

Related U.S. Application Data

(62) Division of application No. 14/031,726, filed on Sep. 19, 2013, now Pat. No. 9,144,678.

(60) Provisional application No. 61/702,876, filed on Sep. 19, 2012, provisional application No. 61/778,501, filed on Mar. 13, 2013.

(51) Int. Cl.
*A61N 1/00* (2006.01)
*A61N 1/36* (2006.01)
*A61N 1/04* (2006.01)

(52) U.S. Cl.
CPC .......... *A61N 1/36014* (2013.01); *A61N 1/0456* (2013.01); *A61N 1/3606* (2013.01); *A61N 1/3605* (2013.01); *A61N 1/36135* (2013.01)

(58) Field of Classification Search
USPC .................................................. 607/62, 115
See application file for complete search history.

(56) References Cited

U.S. PATENT DOCUMENTS

| 7,054,689 B1 | 5/2006 | Whitehurst et al. |
| 7,149,574 B2 | 12/2006 | Yun et al. |
| 2005/0065562 A1 | 3/2005 | Rezai |
| 2005/0143788 A1 | 6/2005 | Yun et al. |
| 2005/0149157 A1* | 7/2005 | Hunter .................. A61K 38/17 607/119 |
| 2010/0198308 A1* | 8/2010 | Zhou .................. A61N 1/3601 607/62 |
| 2011/0137381 A1* | 6/2011 | Lee ....................... A61N 1/0529 607/62 |

* cited by examiner

*Primary Examiner* — Nicole F Lavert
(74) *Attorney, Agent, or Firm* — Tarolli, Sundheim, Covell & Tummino LLP

(57) ABSTRACT

One aspect of the present disclosure relates to a method for treating body organ aging in a mammal. One step of the method includes identifying at least one target organ in need of a therapy signal. Next, a therapy delivery device is placed into electrical communication with an autonomic nervous system (ANS) nerve target and/or a central nervous system (CNS) nerve target associated with the at least one target organ. The therapy delivery device is then activated to deliver the therapy signal to the ANS nerve target and/or the CNS nerve target in an amount and for a time sufficient to effect a change in sympathetic and/or parasympathetic activity associated with the at least one target organ.

14 Claims, 4 Drawing Sheets

APPARATUS, SYSTEMS, AND METHODS FOR TREATING BODY ORGAN AGING

RELATED APPLICATIONS

This application is a Divisional of U.S. patent application Ser. No. 14/031,726, filed Sep. 19, 2013, which claims the benefit of U.S. Provisional Patent Application Ser. Nos. 61/702,876, filed Sep. 19, 2012, and 61/778,501, filed Mar. 13, 2013. The entirety of each of the aforementioned applications is hereby incorporated by reference for ail purposes.

TECHNICAL FIELD

The present disclosure relates generally to neuromodulatory apparatus, systems and methods, and more particularly to apparatus, systems, and methods for treating body organ aging in mammals.

BACKGROUND

The nervous system is a complex, highly specialized network. It organizes, explains, and directs interactions between a subject and the subject's environment. For example, the nervous system controls: sight, hearing, taste, smell and feeling (sensation); voluntary and involuntary functions, such as movement, balance and coordination, as well as blood flow and blood pressure; and the ability to think and reason. The nervous system is divided into the brain and spinal cord (central nervous system) and the nerve cells that control voluntary and involuntary movements (peripheral nervous system or PNS). The PNS is further divided into the sensory-somatic nervous system and the autonomic nervous system (ANS). The ANS regulates the intrinsic function and balance of each body organ, and is always functioning to maintain homeostasis and balance of each organ. Persistent imbalance of the ANS, however, can adversely influence body organ function.

SUMMARY

The present disclosure relates generally to neuromodulatory apparatus, systems and methods, and more particularly to apparatus, systems, and methods for treating body organ aging in mammals.

One aspect of the present disclosure relates to a method for treating body organ aging in a mammal. One step of the method includes identifying at least one target organ in need of a therapy signal. Next, a therapy delivery device is placed into electrical communication with an autonomic nervous system (ANS) nerve target and/or a central nervous system (CNS) nerve target associated with the at least one target organ. The therapy delivery device is then activated to deliver the therapy signal to the ANS nerve target and/or the CNS nerve target in an amount and for a time sufficient to effect a change in sympathetic and/or parasympathetic activity associated with the at least one target organ.

Another aspect of the present disclosure relates to a method for treating body organ aging in a mammal. One step of the method can include determining the level of at least one physiological parameter associated with ANS and/or CNS activity in at least one target organ. Next, dysfunction or degeneration in the target body organ of the mammal can be predicted by comparing the determined level of the at least one physiological parameter with a control value. A therapy delivery device can then be placed into electrical communication with an ANS nerve target and/or CNS nerve target associated with the at least one target organ in a mammal having an abnormal level of the at least one physiological parameter. The therapy delivery device can be activated to deliver the therapy signal to the ANS nerve target and/or the CNS nerve target in an amount and for a time sufficient to effect a change in sympathetic and/or parasympathetic activity associated with the at least one target organ.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
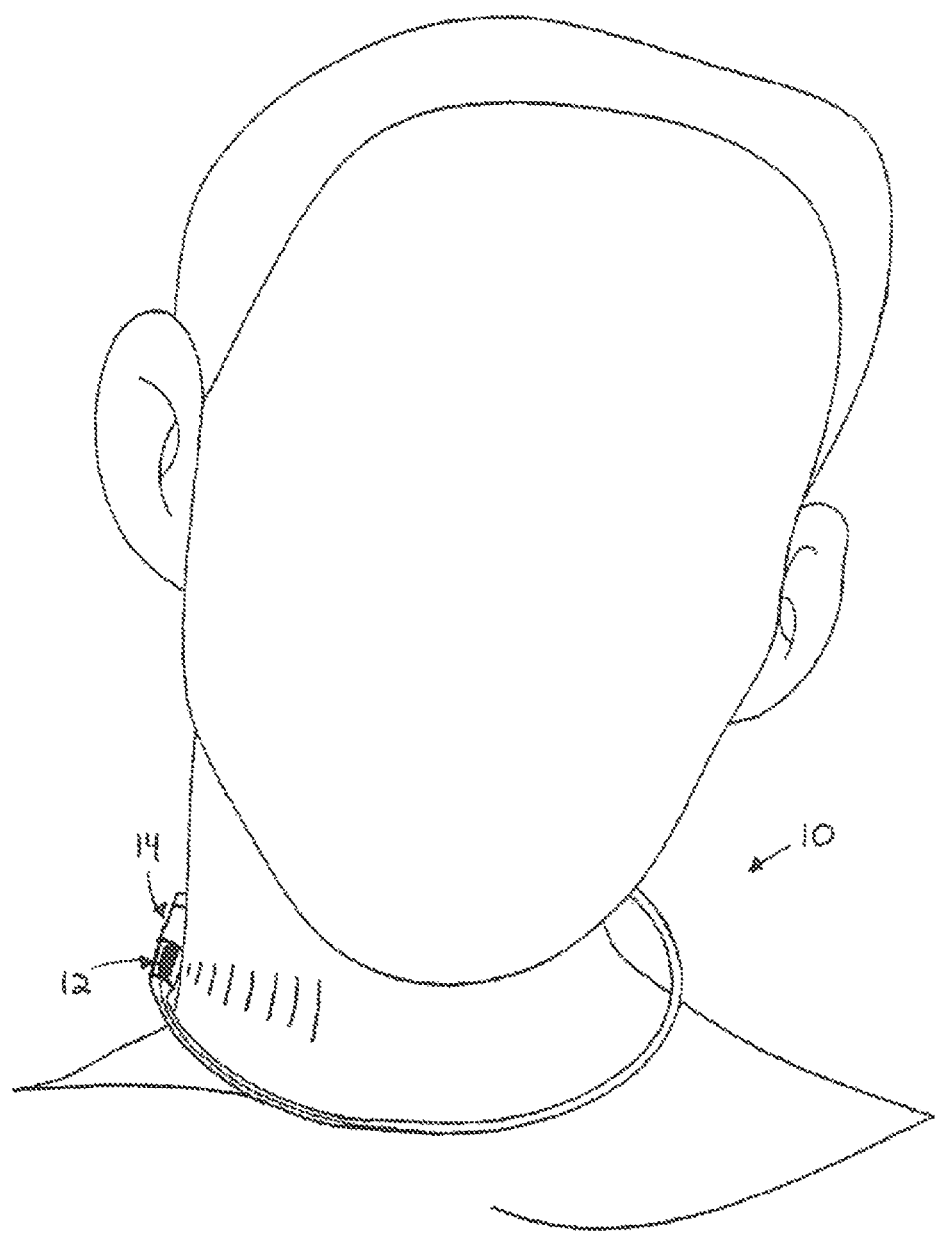
FIG. 1 is a schematic illustration showing a transcutaneous neuromodulatory device constructed in accordance with one aspect of the present disclosure.

Unless defined otherwise, all technical and scientific terms used herein have the same meaning as is commonly understood by one of skill in the art to which the present disclosure pertains.

In the context of the present disclosure, the terms "nervous tissue" or "nerve structure" can refer to any tissues or structures of the autonomic nervous system (ANS) or the central nervous system (CNS) (e.g., brain and spinal cord) including, but not limited to, neurons, axons, fibers, tracts, nerves, plexus, afferent plexus fibers, efferent plexus fibers, ganglion, pre-ganglionic fibers, post-ganglionic fibers, cervical sympathetic ganglialganglion, thoracic sympathetic ganglia/ganglion, afferents, efferents, and combinations thereof.

As used herein, the terms "modulate" or "modulating" with reference to nervous tissue can refer to causing a change in neuronal activity, chemistry, and/or metabolism. The change can refer to an increase, decrease, or even a change in a pattern of neuronal activity. The terms may refer to either excitatory or inhibitory stimulation, or a combination thereof, and may be at least electrical, magnetic, optical or chemical, or a combination of two or more of these. The terms "modulate" or "modulating" can also be used to refer to a masking, altering, overriding, or restoring of neuronal activity.

As used herein, the term "intraluminal target site" can refer to a desired anatomical location at which a therapy delivery device may be positioned. The intraluminal target site can comprise a variety of locations, including intraluminal and extraluminal locations innervated by, or in electrical communication with, nervous tissue. In one example, an intraluminal target site can comprise an intravascular location in electrical communication with at least one nerve of the ANS. Intraluminal target sites contemplated by the present disclosure are described in further detail below.

As used herein, the term "electrical communication" can refer to the ability of an electric field generated by an electrode or electrode array to be transferred, or to have a neuromodulatory effect, within and/or on at least one nerve, neuron, and/or nervous tissue (e.g., of the ANS or CNS).

As used herein, the term "organ" can refer to any anatomical part or tissue having a specific function in a mammal. This also includes a portion of an organ, e.g., a lobe of a lung. In some instances, an organ can include a soft organ, such as a kidney, a liver, a heart, an intestine, a brain, a pancreas or a lung. In other instances, an organ can include a tissue having a specific function, such as the skin, muscle, bone marrow, etc.

As used herein, the terms "treat" or "treating" can refer to therapeutically regulating, preventing, improving, alleviating the symptoms of, reversing and/or reducing the effects of aging in a target organ.

As used herein, the terms "dysfunction" or "degeneration" when used in the context of organ function can refer to a change in organ vital function, leakage of enzymes or substrates from an organ (e.g., into blood or other bodily fluid(s)), and/or abnormal fibrosis.

As used herein, the term "mammal" can refer to any member of the class Mammalia including, without limitation: humans and non-human primates, such as chimpanzees and other apes and monkey species; farm animals or livestock, such as cattle, sheep, pigs, goats and horses; domestic mammals, such as dogs and cats; laboratory animals, such as mice, rats and guinea pigs, and the like. The term does not denote a particular age or sex. Thus, adult and newborn mammals, as well as fetuses, whether male or female, are intended to be included within the scope of this term. Other non-limiting examples of non-human mammals included within the term can include: aardvarks; antelopes; armadillos; badgers; bats; bears; bobcats; buffalo; camels; large cats; cheetahs; civet family; cougars; coyotes; deer; dolphins; donkeys; elephant shrews; elephants; elk; ermine; ferrets; foxes; giraffes; goats; guanacos; hedgehogs; hippopotamuses; hyenas; jaguars; leopards; lions; llamas; lynxes; manatees; marine mammals; marsupials; mink; moles; mongoose family; monotremes; moose; mules; mustelids; ocelots; pine marten; pinnipeds; rabbits; raccoons; pandas; reindeer; caribou; rhinoceroses; rodents; skunks; sloths; solenodons; tapirs; tayras; tigers; vicunas; weasels; whales; wolverine; wolves; yaks; and zebras.

Overview

A brief discussion of the pertinent neurophysiology is provided to assist the reader with understanding certain aspects of the present disclosure. The nervous system is divided into the somatic nervous system and the ANS. In general, the somatic nervous system controls organs under voluntary control (e.g., skeletal muscles) and the ANS controls individual organ function and homeostasis. For the most part, the ANS is not subject to voluntary control. The ANS is also commonly referred to as the visceral or automatic system.

The ANS can be viewed as a "real-time" regulator of physiological functions which extracts features from the environment and, based on that information, allocates an organism's internal resources to perform physiological functions for the benefit of the organism, e.g., responds to environment conditions in a manner that is advantageous to the organism.

The ANS conveys sensory impulses to and from the central nervous system to various structures of the body such as organs and blood vessels, in addition to conveying sensory impulses through reflex arcs. For example, the ANS controls: constriction and dilatation of blood vessels; heart rate; the force of contraction of the heart; contraction and relaxation of smooth muscle in various organs; lungs; stomach; colon; bladder; visual accommodation; and secretions from exocrine and endocrine glands, etc. The ANS does this through a series of nerve fibers, and more specifically through efferent and afferent nerves. The ANS acts through a balance of its two components: the sympathetic nervous system (SNS) and the parasympathetic nervous system (PNS), which are two anatomically and functionally distinct systems. Both of these systems include myelinated preganglionic fibers which make synaptic connections with unmyelinated postganglionic fibers, and it is these fibers which then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands). Each of these is briefly reviewed below.

The PNS is the part of the ANS controlling a variety of autonomic functions including, but not limited to, involuntary muscular movement of blood vessels and gut and glandular secretions from eye, salivary glands, bladder, rectum and genital organs. The vagus nerve is part of the PNS. Parasympathetic nerve fiber are contained within the last five cranial nerves and the last three spinal nerves and terminate at parasympathetic ganglia near or in the organ they supply. The actions of the PNS are broadly antagonistic to those of the SNS—lowering blood pressure, slowing heartbeat, stimulating the process of digestion etc. The chief neurotransmitter in the PNS is acetylcholine. Neurons of the parasympathetic nervous system emerge from the brainstem as part of the Cranial nerves III, VII, IX and X (vagus nerve) and also from the sacral region of the spinal cord via Sacral nerves. Because of these origins, the PNS is often referred to as the "craniosacral outflow".

In the PNS, both pre- and post-ganglionic neurons are cholinergic (i.e., they utilize the neurotransmitter acetylcholine). Unlike adrenaline and noradrenaline, which the body takes around 90 minutes to metabolize, acetylcholine is rapidly broken down after release by the enzyme cholinesterase. As a result the effects are relatively brief in comparison to the SNS.

Each pre-ganglionic parasympathetic neuron synapses with just a few post-ganglionic neurons, which are located near, or in, the effector organ, a muscle or gland. As noted above, the primary neurotransmitter in the PNS is acetylcholine such that acetylcholine is the neurotransmitter at all the pre- and many of the post-ganglionic neurons of the PNS. Some of the post-ganglionic neurons, however, release nitric oxide as their neurotransmitter.

The SNS is the part of the ANS comprising nerve fibers that leave the spinal cord in the thoracic and lumbar regions and supply viscera and blood vessels by way of a chain of sympathetic ganglia running on each side of the spinal column which communicate with the central nervous system via a branch to a corresponding spinal nerve. The SNS controls a variety of autonomic functions including, but not limited to, control of movement and secretions from viscera and monitoring their physiological state, stimulation of the sympathetic system inducing, e.g., the contraction of gut sphincters, heart muscle and the muscle of artery walls, and the relaxation of gut smooth muscle and the circular muscles of the iris. The chief neurotransmitter in the SNS is adrenaline, which is liberated in the heart, visceral muscle, glands and internal vessels, with acetylcholine acting as a neurotransmitter at ganglionic synapses and at sympathetic terminals in skin and skeletal muscles. The actions of the SNS tend to be antagonistic to those of the PNS.

The neurotransmitter released by the post-ganglionic neurons is nonadrenaline (also called norepinephrine). The action of noradrenaline on a particular structure, such as a gland or muscle, is excitatory in some cases and inhibitory in others. At excitatory terminals, ATP may be released along with noradrenaline. Activation of the SNS may be characterized as general because a single pre-ganglionic neuron usually synapses with many post-ganglionic neurons, and the release of adrenaline from the adrenal medulla into the blood ensures that all the cells of the body will be exposed to sympathetic stimulation even if no post-ganglionic neurons reach them directly.

The present disclosure relates generally to neuromodulatory apparatus, systems and methods, and more particularly to apparatus, systems, and methods for organ aging in a mammal. Body organ degeneration and aging is a complex process governed by genetics and environmental influences. The progressive deterioration and dysfunction of an organ can be manifested by a decrease in the purposeful output of the organ, or a decrease in responsiveness and adaptation of the organ to environmental influences. The ANS regulates the intrinsic function and balance of each body organ, and constantly functions to maintain the homeostasis and balance of each organ. Over time, however, the inherent tone and influence of the ANS on specific body organs can be reduced and thereby impair or limit the function and effectiveness of the organ(s). As described in detail below, the present disclosure advantageously provides apparatus, systems, and methods for precise and selective control of the ANS and/or CNS to effectively normalize or regulate the inherent tone and influence of the ANS and/or CNS to treat body organ aging. As opposed to conventional wisdom, which dictates that aging leads to nervous system dysfunction, the present disclosure is based, at least in part, on the notion that nervous system (e.g., ANS and/or CNS) dysfunction directly leads to aging and organ dysfunction and, therefore, that such dysfunction can be reversed by precise and selective control of the ANS and/or CNS.

Therapy Delivery Devices

In one aspect, the present disclosure includes various therapy delivery devices (not shown) and related systems configured to treat organ aging in a mammal. In some instances, therapy delivery devices that may be used to practice the present disclosure may be positioned directly on a target nerve, neuron or nerve structure. In other instances, therapy delivery devices that may be used to practice the present disclosure may be positioned below the skin of a mammal but not directly on a target nerve, neuron or nerve structure. In further instances, therapy delivery devices that may be used to practice the present disclosure may comprise an external device, e.g., positioned in a lumen adjacent a target nerve, neuron or nerve structure. In still further instances, therapy delivery devices used to practice the present disclosure can include an external device, e.g., positioned on the skin of a mammal adjacent a target nerve, neuron or nerve structure. Therapy delivery devices can be temporarily or permanently implanted within, on, or otherwise associated with a mammal suffering from, or afflicted by, organ dysfunction or degeneration as a result of aging.

Therapy delivery devices of the present disclosure can be configured to deliver various types of therapy signals to a target nerve, neuron or nerve structure. For example, therapy delivery devices of the present disclosure can be configured to deliver only electrical energy, only a pharmacological or biological agent, or a combination thereof. In one example, therapy delivery devices of the present disclosure can comprise at least one electrode and an integral or remote electrical energy generator (not shown), which is in electrical communication with the one or more electrodes and configured to produce one or more electrical signals (or pulses). In another example, therapy delivery devices can include a pharmacological or biological agent reservoir, a pump, and a fluid dispensing mechanism. Non-limiting examples of pharmacological and biological agents can include chemical compounds, drugs, nucleic acids, polypeptides, stem cells, toxins (e.g., botulinum), as well as various energy forms, such as ultrasound, radiofrequency (continuous or pulsed), magnetic waves, cryotherapy, and the like. In yet another example, therapy delivery devices can be configured to deliver magnetic nerve stimulation with desired field focality and depth of penetration. One skilled in the art will appreciate that combinations of the therapy delivery devices above configurations are also included within the scope of the present disclosure.

In some instances, therapy delivery devices can include a stimulator (or inhibitor), such as an electrode, a controller or programmer, and one or more connectors for connecting the stimulating (or inhibiting) device to the controller. In further describing representative electrodes, which are described in the singular, it will be apparent that more than one electrode may be used as part of a therapy delivery device. Accordingly, the description of a representative electrode suitable for use in the therapy delivery devices of the present disclosure is applicable to other electrodes that may be employed.

An electrode can be controllable to provide output signals that may be varied in voltage, frequency, pulse-width, current and intensity. The electrode can also provide both positive and negative current flow from the electrode and/or is capable of stopping current flow from the electrode and/or changing the direction of current flow from the electrode. In some instances, therapy delivery devices can include an electrode that is controllable, i.e., in regards to producing positive and negative current flow from the electrode, stopping current flow from the electrode, changing direction of current flow from the electrode, and the like. In other instances, the electrode has the capacity for variable output, linear output and short pulse, width.

The electrical energy generator can comprise a battery or generator, such as a pulse generator that is operatively connected to the electrode. For example, the electrical energy generator can include a battery that is rechargeable by inductive coupling. The electrical energy generator may be positioned in any suitable location, such as adjacent the electrode (e.g., implanted adjacent the electrode), or a remote site in or on the mammal's body or away from the mammal's body in a remote location. An electrode may be connected to the remotely positioned electrical energy generator using wires, e.g., which may be implanted at a site remote from the electrode or positioned outside the mammal's body. In one example, implantable electrical energy generators analogous to a cardiac pacemaker may be used.

The electrical energy generator can control the pulse waveform, the signal pulse width, the signal pulse frequency, the signal pulse phase, the signal pulse polarity, the signal pulse amplitude, the signal pulse intensity, the signal pulse duration, and combinations thereof of an electrical signal. The electrical energy generator may be used to convey a variety of currents and voltages to one or more electrodes and thereby modulate the activity of a nerve, neuron, or nerve structure. The electrical energy generator may be used to control numerous electrodes independently or in various combinations as needed to provide stimulation. In some instances, an electrode may be employed that includes its own power source, e.g., which is capable of obtaining sufficient power for operation from surrounding tissues in the mammal's body, or which may be powered by bringing a power source external to the mammal's body into contact with the mammal's skin, or which may include an integral power source.

In other instances, an electrical signal may be constant, varying and/or modulated with respect to the current, voltage, pulse-width, cycle, frequency, amplitude, and so forth. For example, a current may range from about 0.001 to about 1000 microampere (mA) and, more specifically, from about 0.1 to about 100 mA. Similarly, the voltage may range from about 0.1 millivolt to about 25 volts, or about 0.5 to about 4000 Hz, with a pulse-width of about 10 to about 1000 microseconds. The type of stimulation may vary and involve different waveforms known to the skilled artisan. For example, the stimulation may be based on the H waveform found in nerve signals (i.e., Hoffman Reflex). In another example, different forms of interferential stimulation may be used.

To increase activity in a portion of the ANS, for example, voltage or intensity may range from about 1 millivolt to about 1 volt or more, e.g., 0.1 volt to about 50 volts (e.g., from about 0.2 volt to about 20 volts), and the frequency may range from about 1 Hz to about 2500 Hz, e.g., about 1 Hz to about 1000 Hz (e.g., from about 2 Hz to about 100 Hz). In some instances, pure DC and/or AC voltages may be employed. The pulse-width may range from about 1 microsecond to about 2000 microseconds or more, e.g., from about 10 microseconds to about 2000 microseconds (e.g., from about 15 microseconds to about 1000 microseconds). The electrical signal may be applied for at least about 1 millisecond or more, e.g., about 1 second (e.g., about several seconds). In some instances, stimulation may be applied for as long as about 1 minute or more, e.g., about several minutes or more (e.g., about 30 minutes or more).

To decrease activity in a portion of the ANS, for example, voltage or intensity may range from about 1 millivolt to about 1 volt or more, e.g., 0.1 volt to about 50 volts (e.g., from about 0.2 volt to about 20 volts), and the frequency may range from about 1 Hz to about 2500 Hz, e.g., about 50 Hz to about 2500 Hz. In some instances, pure DC and/or AC voltages may be employed. The pulse-width may range from about 1 microseconds to about 2000 microseconds or more, e.g., from about 10 microseconds to about 2000 microseconds (e.g., from about 15 microseconds to about 1000 microseconds). The electrical signal may be applied for at least about 1 millisecond or more, e.g., about 1 second (e.g, about several seconds). In some instances, the electrical energy may be applied for as long as about 1 minute or more, e.g., about several minutes or more (e.g., about 30 minutes or more may be used).

The electrode may be mono-polar, bipolar or multi-polar. To minimize the risk of an immune response triggered by the mammal against the therapy delivery device, and also to minimize damage thereto (e.g., corrosion from other biological fluids, etc.), the electrode (and any wires and optional housing materials) can be made of inert materials, such as silicon, metal, plastic and the like. In one example, a therapy delivery device can include a multi-polar electrode having about four exposed contacts (e.g., cylindrical contacts).

A controller or programmer may also be associated with a therapy delivery device. A programmer, for example, can include one or more microprocessors under the control of a suitable software program. Other components of a programmer, such as an analog-to-digital converter, etc., will be apparent to those of skill in the art.

Therapy delivery devices can be pre-programmed with desired stimulation parameters. Stimulation parameters can be controllable so that an electrical signal may be remotely modulated to desired settings without removal of the electrode from its target position. Remote control may be performed, e.g., using conventional telemetry with an implanted electric signal generator and battery, an implanted radiofrequency receiver coupled to an external transmitter, and the like. In some instances, some or all parameters of the electrode may be controllable by the subject, e.g., without supervision by a physician. In other instances, some or all parameters of the electrode may be automatically controllable by a programmer or controller comprising the therapy delivery device.

In one example, the therapy delivery device can be configured for percutaneous placement or implantation. In this instance, the therapy delivery device can comprise one or more implantable electrodes shaped or configured, for example, as a wire, a rod, a filament, a ribbon, a cord, a tube, a formed wire, a flat strip, or a combination thereof. In one example, one or more of the electrodes can comprise a laminotomy electrode array. Laminotomy electrodes, for example, generally have a flat paddle configuration and typically possess a plurality of electrodes (e.g., 2, 3, 4 or more) arranged on the paddle. The arrangement of electrodes on the paddle may be in rows and columns, staggered, spaced, circular, or any other arrangement that will position the electrodes for optimal delivery of electrical energy. The one or more implantable electrodes may be controlled individually, in series, in parallel, or any other manner desired. Once implanted, the implantable electrode(s) may be held in position using any method known to the skilled artisan, such as stitches, epoxy, tape, glue, sutures, or a combination thereof.

In another example the therapy delivery device can be configured for deep brain stimulation (DBS). Examples of therapy delivery devices that may be configured for DBS are disclosed in U.S. Pat. Nos. 7,623,927, 8,190,263 and 7,697,991 to Rezai et al.

In another example, the therapy delivery device can be configured for intravascular or intraluminal placement or implantation. In some instances, a therapy delivery device configured for intravascular or intraluminal placement or implantation can be configured in an identical or similar manner as the expandable electrode disclosed in U.S. patent application Ser. No. 11/641,331 to Greenberg et al. (hereinafter, "the '331 application").

In yet another example, the therapy delivery device can be configured for transcutaneous neuromodulation. In some instances, transcutaneous neuromodulation can include positioning an electrode on a skin surface so that a therapy signal can be delivered to a target nerve, neuron, or nerve structure. Transcutaneous neuromodulation can additionally include partially transcutaneous methods (e.g., using a fine, needle-like electrode to pierce the epidermis). In other instances, a surface electrode can be placed into electrical contact with a nerve, neuron, or nerve structure (e.g., of the ANS) associated with a target organ. Generally, an electrical signal used for transcutaneous neuromodulation may be constant, varying and/or modulated with respect to the current, voltage, pulse-width, cycle, frequency, amplitude, and so forth (e.g., the current may be between about 1 to 100 microampere), about 10 V (average), about 1 to about 1000 Hz, with a pulse-width of about 250 to about 500 microseconds.

In one example, a transcutaneous neuromodulation device can comprise a wearable accessory item, such as a necklace or collar 10 (FIG. 1). As shown in FIG. 1, a necklace or collar 10 can be configured to include at least one electrode 12 for delivering a therapy signal to a particular region of a subject's neck (e.g., an anterior or posterior region thereof) depending upon the target organ(s). The necklace or collar 10 can additionally include an integral power source 14 (e.g., a rechargeable battery). It will be appreciated that the electrode(s) 12 can alternatively be powered by a wireless power source (not shown). In other instances, the electrode 14 can comprise a coil configured to deliver magnetic stimulation. The necklace or collar 10 can be configured to obtain a pre-selected position about a subject's neck by, for example, using a positioning guide (not shown), weighting the necklace or collar, etc. Alternatively, the subject can manually adjust the necklace or collar 10 as needed to optimize delivery of the therapy signal from the electrode(s) 12 to an ANS nerve target and/or CNS nerve target. Other examples of wearable accessory items that can be configured as a transcutaneous neuromodulation device include pendants, buttons, earrings, etc.

Figure 2A:
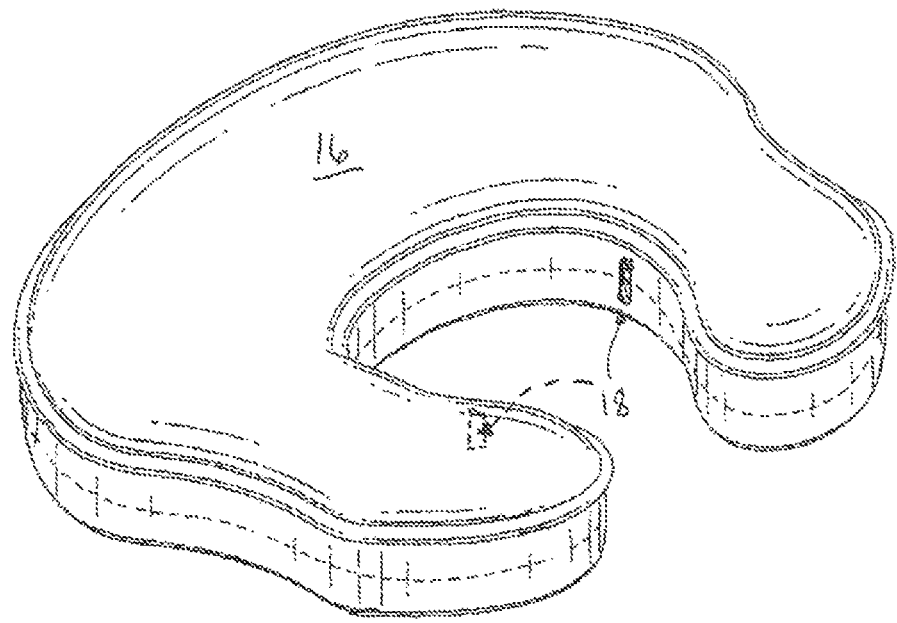
FIGS. 2A-B are schematic illustrations showing transcutaneous neuromodulatory devices constructed in accordance with another aspect of the present disclosure.
Figure 2B:
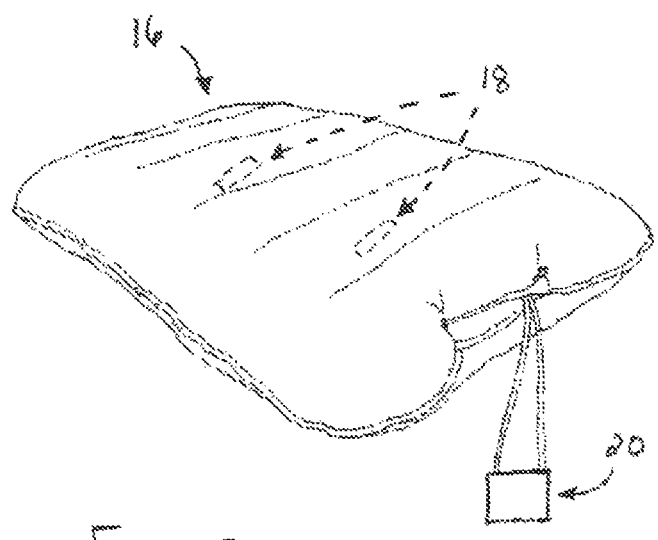

In another example, a transcutaneous neuromodulation device can comprise a pillow 16 (FIGS. 2A-B). In some instances, the pillow 16 (FIG. 2A) can be configured as a collar for use in a reclined or upright position, such as on an airplane, in a car, on a couch, etc. The pillow 16 can include at least one electrode 18 configured to deliver a therapy signal to an ANS nerve target and/or a CNS nerve target (e.g., in a subject's head or neck). As shown in FIG. 2A, the pillow 16 includes two oppositely disposed electrodes 18. The pillow 16 can also include a power source (not shown), which may be integrally connected with the pillow or located remotely (i.e., wirelessly) therefrom. In other instances, the pillow 16 (FIG. 2B) can comprise a traditional or conventional pillow for use when a subject is sleeping or lying in bed. As shown in FIG. 2I, the pillow 16 can include two oppositely disposed electrodes 18 configured to deliver a therapy signal to a target nerve when the subject neck or head is straddled between the electrodes. The pillow 16 can further include a power source 20 that is in direct electrical communication with the electrodes 18; however, it will be appreciated that the power source can be located remotely (i.e., wirelessly) from the pillow.

In yet another example, a therapy delivery device can be configured for transcutaneous neuromodulation using magnetic stimulation. A magnetic stimulation device or system can generally include a pulse generator (e.g., a high current pulse generator) and a stimulating coil capable of producing magnetic pulses with desired field strengths. Other components of a magnetic stimulation device can include transformers, capacitors, microprocessors, safety interlocks, electronic switches, and the like. In operation, the discharge current flowing through the stimulating coil can generate the desired magnetic field or lines of force. As the lines of force cut through tissue (e.g., neural tissue), a current is generated in that tissue. If the induced current is of sufficient amplitude and duration such that the cell membrane is depolarized, nervous tissue will be stimulated in the same manner as conventional electrical stimulation. It is therefore worth noting that a magnetic field is simply the means by which an electrical current is generated within the nervous tissue, and that it is the electrical current, and not the magnetic field, which causes the depolarization of the cell membrane and thus stimulation of the target nervous tissue. Thus, in some instances, advantages of magnetic over electrical stimulation can include: reduced or sometimes no pain; access to nervous tissue covered by poorly conductive structures; and stimulation of nervous tissues lying deeper in the body without requiring invasive techniques or very high energy pulses.

Other examples of transcutaneous therapy delivery devices and systems that may be used as part of the present disclosure are described in U.S. Provisional Patent Application Ser. No. 61/693,946, filed Sep. 19, 2012, and U.S. patent application Ser. No. 14/011,133, filed Aug. 27, 2013. It will be appreciated that transcutaneous therapy delivery devices and systems can additionally or optionally include any wearable item, accessory, article of clothing, or any object, device, or apparatus that a subject can use and, during use, comes into close or direct contact with a portion of the subject's body (e.g., the subject's neck). Examples of such transcutaneous neuromodulation devices can include vests, sleeves, shirts, socks, shoes, underwear, belts, scarves, wrist bands, gloves, car pieces, hand-aids, turtle neck, pendants, buttons, earrings, stickers, patches, bio-films, skin tattoos (e.g., using neuropaint), chairs, computers, beds, head rests (e.g., of a chair or car seat), cell phones, and the like.

Therapy delivery devices can be part of an open- or closed-loop system. In an open-loop system, for example, a physician or subject may, at any time, manually or by the use of pumps, motorized elements, etc., adjust treatment parameters, such as pulse amplitude, pulse-width, pulse frequency, duty cycle, dosage amount, type of pharmacological or biological agent, etc. Alternatively, in a closed-loop system, treatment parameters (e.g., electrical signals) may be automatically adjusted in response to a sensed physiological parameter or a related symptom indicative of the extent and/or presence of organ degeneration or dysfunction associated with aging. In a closed-loop feedback system, a sensor (not shown) that senses a physiological parameter associated with organ aging can be utilized. More detailed descriptions of sensors that may be employed in a closed-loop system, as well as other examples of sensors and feedback control techniques that may be employed as part of the present disclosure are disclosed in U.S. Pat. No. 5,716,377. In one example, a sensor for use as part of a closed-loop system can be configured for implantation on or within a mammal suffering from, or that is suspected of suffering from, organ degeneration or dysfunction associated with aging.

It should be appreciated that incorporating a therapy delivery device as part of a closed-loop system can include placing or implanting a therapy delivery device on or within a mammal at an ANS nerve target and/or CNS nerve target associated with a dysfunctional or degenerate target organ (or organs), sensing a physiological parameter associated with the target organ(s), and then activating the therapy delivery device to apply a therapy signal to adjust application of the therapy signal to the ANS nerve target and/or CNS nerve target in response to the sensor signal to treat the target organ(s). Non-limiting examples of physiological parameters associated with a dysfunctional or degenerate target organ (or organs) are provided in Table 1 (below).

Methods

Another aspect of the present disclosure includes methods for treating body organ aging in a mammal. In general, methods of the present disclosure can include the steps of: identifying at least one target organ in need of a therapy signal; providing a therapy delivery device; placing the therapy delivery device into electrical communication with an ANS nerve target and/or CNS nerve target associated with the at least one target organ; and activating the therapy delivery device to deliver the therapy signal to the ANS nerve target and/or CNS nerve target in an amount and for a time sufficient to effect a change in sympathetic and/or parasympathetic activity associated with the target organ(s). Mammals treatable by the present disclosure can, in some instances, have two or more target organs in need of a therapy signal. Target organs treatable by the present disclosure can include organs whose function (e.g., output, responsiveness, etc.) is diminished or decreased as a result of abnormal autonomic activity.

In one example, target organs treatable by the present disclosure can include organs whose function is diminished or decreased as a result of hyposympathetic tone or activity.

Figure 3:
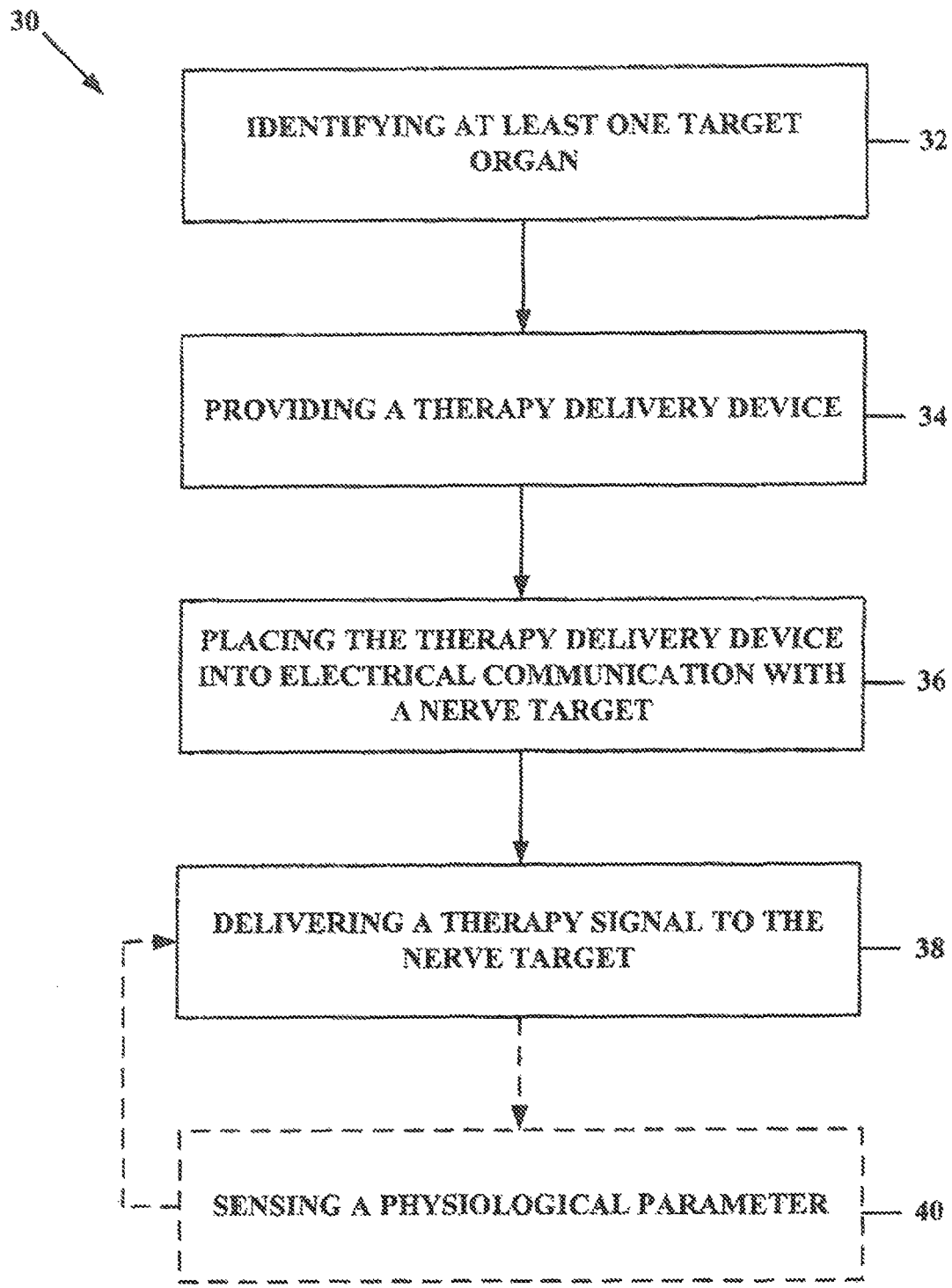
FIG. 3 is a process flow diagram illustrating a method for treating body organ aging in a mammal according to another aspect of the present disclosure.

As shown in FIG. 3, one step of the method 30 can include identifying at least one target organ in need of a therapy signal (Step 32). Target organs can be identified based on any one or combination of medical diagnostic assays or techniques. In some instances, a target organ can be identified based on an abnormal level (as compared to a control value) of one or more physiological parameters. Non-limiting examples of physiological parameters that may be used to identify a target organ can include those listed in Table 1.

TABLE 1

Target Nerve Structures, Target Organs, and Physiological Parameters

| Target Nerve Structures | Target Organ | Physiological Parameters |
|---|---|---|
| (1) sympathetic chain ganglia and related pre-ganglionic and post-ganglionic nerve structures, such as a superior sympathetic chain ganglion, a middle sypathetic chain ganglion, an inferior sympathetic chain ganglion, a stellate ganglion, and a thoracic sympathetic chain ganglion (e.g., at the level of T2-T6): (2) spinal cord (e.g., cervical and thoracic segments) and dorsal root ganglia; (3) peripheral nerves; (4) somatic motor and sensory nerves; (5) parasympathetic nerve structures, such as the vagus nerve; and (6) autonomic plexuses, such as the pulmonary plexus. | Lungs | (1) output/data from high resolution computed tomopgraphy (HRCT); (2) output/data from pulmonary function tests (e.g., spirometry, lung volume, etc.); (3) lung biopsies (e.g., showing fibrosis); (4) peripheral blood markers of inflammation; (5) nitrous oxide; (6) RR interval; (7) oxygen saturation; and (8) other exhaled markers, such as those disclosed in U.S. Pat. No. 8,155,744 to Rezai et al. |
| Cerebral regions, including epidural regions, subdural regions, and intracerebral regions (e.g., hypothalamus, brain stem nuclei, ventral capsule/ventral striatum, dorsolateral prefrontal cortex, dorsomedial prefrontal cortex, oculomotor complex, and mesial, dorsal and lateral cortex). | Brain | (1) output/data from MRI with contrast; (2) output/data from functioning imaging (e.g., EEG, PET, etc.) (3) evoked potentials (e.g., somatosensory evoked potentials); and (4) hormones (e.g., cortisol). |
| (1) sympatheic chain ganglia and related pre-ganglionic and post-ganglionic nerve structures, such as a superior sympathetic chain ganglion, a middle sypathetic chain ganglion, an inferior sympathetic chain ganglion, a stellate ganglion, and a thoracic sympathetic chain ganglion (e.g., at the level of T2-T10); (2) spinal cord (e.g., cervical and thoracic segments) and dorsal root ganglia; (3) peripheral nerves; (4) somatic motor and sensory nerves; (5) parasympathetic nerve structures, such as the vagus nerve; and (6) autonomic plexuses, such as the pulmonary plexus and the cardiac plexus. | Heart | (1) output/data from 2D echocardiogram; (2) output/data from MRI; (3) brain natriuretic peptide; (4) C-reactive protein; (5) EKG; and (6) RR interval. |
| (1) sympathetic chain ganglia and related pre-ganglionic and post-ganglionic nerve structures, such as a superior sympathetic chain ganglion, a middle sympathetic chain ganglion, an inferior sympathetic chain ganglion, a stellate ganglion, and a lumbosacral ganglion; (2) spinal cord (e.g., cervical and thoracic segments) and dorsal root ganglia; (3) peripheral nerves; (4) somatic motor and sensory nerves; (5) parasympathetic nerve structures, such as the posterior vagal trunk; and (6) other autonomic ganglia and plexuses, such as celiac plexus and ganglion, superior and inferior mesenteric ganglia, phremic ganglion, splanchmic nerves, aortico-renal ganglion, and lesser and greater splanchnic nerves. | Skin | (1) loss of elasticity; (2) biopsy; (3) thermography; (4) sweating; (5) tone; and (6) turgor. |
| (1) sympathetic chain ganglia and related pre-ganglionic and post-ganglionic nerve structures, such as a superior sympathetic chain ganglion, a middle sympathetic chain ganglion, an inferior sympathetic chain ganglion, a stellate ganglion, a thoracic sypathetic chain ganglionic, and a lumbosacral ganglion; (2) spinal cord (e.g., cervical and thoracic segments) and dorsal root ganglia; (3) peripheral nerves; (4) somatic motor and sensory nerves; (5) parasympathetic nerve structures, such as the posterior vagal trunk; and | Muscles | (1) weakness; (2) biopsy; (3) EMG; (4) thermography; (5) tone; and (6) turgor. |

TABLE 1-continued

Target Nerve Structures, Target Organs, and Physiological Parameters

| Target Nerve Structures | Target Organ | Physiological Parameters |
|---|---|---|
| (6) other autonomic ganglia and plexuses, such as celiac plexus and ganglion, superior and inferior mesenteric ganglia, phrenic ganglion, splanchnic nerves, aortico-renal ganglion, and lesser and greater splanchnic nerves. | | |
| (1) sympathetic chain ganglia and related pre-ganglionic and post-ganglionic nerve structures, such as a superior sympathetic chain ganglion, a middle sympathetic chain ganglion, an inferior sympathetic chain ganglion, a stellate ganglion, a thoracic sypathetic chain ganglionic, and a lumbosacral ganglion; (2) spinal cord (e.g., cervical and thoracic segments) and dorsal root ganglia; (3) peripheral nerves; (4) somatic motor and sensory nerves; (5) parasympathetic nerve structures, such as the posterior vagal trunk; and (6) other autonomic ganglia and plexuses, such as celiac plexus and ganglion, pulmonary plexus, superior and inferior mesenteric ganglia, phrenic ganglion, splanchnic nerves, aortico-renal ganglion, renal ganglia, and lesser and greater splanchnic nerves. | Kidneys | (1) output/data from CT; (2) renal biopsy; (3) uric acid; (4) output/data from ultrasound; (5) anti-diuretic hormone; (6) oxytocin; (7) kidney hormones (e.g., erthropoietin), and (8) adreno-cortico-tropic-hormone. |
| (1) sympathetic chain ganglia and related pre-ganglionic and post-ganglionic nerve structures, such as a superior sympathetic chain ganglion, a middle sympathetic chain ganglion, an inferior sympathetic chain ganglion, a stellate ganglion, a thoracic sypathetic chain ganglionic, and a lumbosacral ganglion; (2) spinal cord (e.g., cervical and thoracic segments) and dorsal root ganglia; (3) peripheral nerves; (4) somatic motor and sensory nerves; (5) parasympathetic nerve structures, such as the posterior vagal trunk; and (6) other autonomic ganglia and plexuses, such as celiac plexus and ganglion, pulmonary plexus, superior and inferior mesenteric ganglia, phrenic ganglion, splanchnic nerves. | Liver | (1) output/data from CT; (2) output/data from MRI; (3) hormones (e.g., IGF-1); (4) liver function tests (e.g., Alb, ALT, AST, ALP, TBH, GGT, etc.); (5) insulin; and (6) glucagon. |

After identifying at least one target organ in need of a therapy signal, a therapy delivery device can be provided (Step 34) and placed into electrical communication with an ANS nerve target and/or a CNS nerve target associated with the at least one target organ (Step 36). In some instances, Step 36 can entail different surgical and/or medical techniques, depending upon the ANS nerve target or the CNS nerve target. In some instances, a therapy delivery device can be surgically placed into electrical communication with an ANS nerve target and/or a CNS nerve target via a percutaneous or endoscopic route. In other instances, a therapy delivery device can be placed into electrical communication with an ANS nerve target and/or a CNS nerve target via an intravascular or intraluminal route. In further instances, a therapy delivery device can be placed into electrical communication with an ANS nerve target and/or CNS nerve target via a transcutaneous approach. In still further instances, a therapy delivery device can be placed into electrical communication with a CNS nerve target via a DBS approach.

Examples of ANS and/or CNS nerve targets into which a therapy delivery device may be placed in electrical communication are listed in Table 1.

In one example, a therapy delivery device can be placed into electrical communication with an ANS and/or CNS nerve target of a human.

In another example, a therapy delivery device can be placed into electrical communication with an ANS and/or CNS nerve target of a domesticated animal (e.g., a pet) or livestock.

After placing the therapy delivery device, the therapy delivery device can be activated to deliver a therapy signal to the ANS nerve target and/or CNS nerve target in an amount and for a time sufficient to effect a change in sympathetic and/or parasympathetic activity associated with the target organ(s) (Step 38). In some instances, the therapy signal can include an electrical signal capable of electrically modulating the ANS nerve target and/or CNS nerve target. In one example, the therapy signal can include an electrical signal capable of electrically modulating at least a portion of the ANS, at least a portion of the CNS, or a combination thereof. Electrical modulation of the ANS, for example, may affect central motor output, nerve conduction, neurotransmitter release, synaptic transmission, and/or receptor activation. In some instances, at least a portion of the ANS may be electrically modulated to alter, shift, or change parasympathetic activity from a first state to a second state, where the second state is characterized by an increase or decrease in parasympathetic activity relative to the first state. Alternatively, at least a portion of the ANS may be electrically modulated to alter, shift, or change sympathetic activity from a first state to a second state, where the second state is characterized by an increase or decrease in sympathetic activity relative to the first state.

It will be appreciated that delivering electrical energy, for example, to an ANS nerve target can modulate the ANS in any desirable combination of ways, such as increasing both parasympathetic and sympathetic activity, increasing parasympathetic activity while decreasing sympathetic function, decreasing both parasympathetic and sympathetic activity, decreasing parasympathetic activity while increasing sympathetic activity, and increasing sympathetic activity (e.g., from a hyposympathetic state) while maintaining parasympathetic activity.

One example of the method 30 can entail transvascular or transluminal delivery of one or more therapy signals (e.g., electrical energy) to an ANS nerve target associated with a dysfunctional or degenerate target organ. Thus, in some instances, the method 30 can include providing a therapy delivery device configured for transvascular or transluminal insertion and placement within the mammal. For instance, a therapy delivery device configured for intravascular or intraluminal placement in a mammal can include an expandable electrode as disclosed in the '331 application. The therapy delivery device can be inserted into a vessel or lumen of the mammal. Non-limiting examples of vessel and lumens into which the therapy delivery device can be inserted include arteries, veins, an esophagus, a trachea, a vagina, a rectum, an ear canal, an oral cavity, or any other bodily orifice. The therapy delivery device can be surgically inserted into the vessel or lumen via a percutaneous, transvascular, laparoscopic, or open surgical procedure.

After inserting the therapy delivery device into the vessel or lumen, the therapy delivery device can be advanced (if needed) to an intraluminal target site of the ANS and placed into electrical communication therewith. In some instances, advancement of the therapy delivery device can be done under image guidance (e.g., fluoroscopy, CT, MRI, etc.). Intraluminal target sites can include intravascular or intraluminal locations at which the therapy delivery device can be positioned. For example, an intraluminal target site can include a portion of a vessel wall that is innervated by (or in electrical communication with) a nerve, neuron, and/or nervous tissue of the ANS. Examples of intraluminal target sites are listed in Table 1.

The therapy delivery device can be activated to deliver a therapy signal to the intraluminal target site in an amount and for a time sufficient to effect a change in sympathetic and/or parasympathetic activity associated with the target organ(s). In some instances, sympathetic activity can be increased to reverse or mitigate loss of nervous system resilience (e.g., sympathetic tone). Loss of nervous system resilience can be measured by loss of heart rate variability. Thus, in one example, a therapy signal (e.g., electrical energy) can be delivered to an ANS nerve target (e.g., cardiac plexus) in an amount and for a time sufficient to increase sympathetic activity associated with the heart of a mammal. In doing so, heart rate variability in the mammal can be increased (e.g., to a normal or control value) over a period of time.

In another example of the present disclosure, the method 30 can include providing a therapy delivery device configured for placement and implantation within the mammal. In one example, the therapy delivery device can comprise an electrode array configured for percutaneous implantation in the mammal. The therapy delivery device can be placed into direct electrical contact with an ANS nerve target associated with a target organ (or organs). In some instances, "direct electrical contact" can mean that the therapy delivery device is placed on or in the ANS nerve target. In other instances, "direct electrical contact" can mean that the therapy delivery device is located adjacent (but not in physical contact with) the ANS nerve target such that delivery of a therapy signal can modulate a function, activity, and/or characteristic of the ANS nerve target. Examples of ANS nerve targets are listed in Table 1.

After placing the therapy delivery device into direct electrical contact with the ANS nerve target, a therapy signal can be delivered to the ANS nerve target. The therapy signal can be delivered in an amount and for a time sufficient to effect a change in sympathetic and/or parasympathetic activity in the mammal. In some instances, loss of nervous system resilience can manifest as presbyopia. Thus, in one example, the ANS nerve target can include a sympathetic and/or parasympathetic fiber that innervates the ciliary muscle. The ciliary muscle controls the shape of the lens through suspended ligaments called zonules, which provides the accommodation ability to the eye. Like most smooth muscles, the ciliary muscle has a dual innervation, receiving both sympathetic and parasympathetic fibers. In the ciliary muscle, the contraction necessary for accommodation is under parasympathetic control. In the natural resting state of the eye, the parasympathetic system maintains ciliary muscle tone, i.e., the ciliary muscle is contracted and zonular tension is relaxed such that the lens is more spherical and in a forward position increasing the refractive power of the eye. Thus, in one example, a therapy signal (e.g., an electrical signal) can be delivered to a parasympathetic fiber associated with a ciliary muscle in an amount and for a time sufficient to modulate parasympathetic activity and thereby promote contraction necessary for normal accommodation of the eye and restoration of lost vision.

In yet another example of the present disclosure, the method 30 can include providing a therapy delivery device configured for placement on the skin of the mammal. Examples of therapy delivery devices configured for transcutaneous delivery of one or more therapy signals are described above. In some instances, the therapy delivery device can be positioned about the mammal, without penetrating the skin of the mammal, so that the therapy delivery device is in electrical communication with one or more ANS and/or CNS nerve targets associated with a target organ. Non-limiting examples of ANS and CNS nerve targets into which the therapy delivery device can be placed into electrical communication are provided in Table 1.

After appropriately positioning the therapy delivery device, a therapy signal can be delivered from the therapy delivery device to one or more ANS and/or CNS nerve targets associated with the target organ. The therapy signal can be delivered in an amount and for a time sufficient to effect a change in sympathetic and/or parasympathetic activity associated with the target organ. In one example, a therapy signal (e.g., electrical energy) can be transcutaneously delivered to a nerve structure associated with renal function, such as an aortico-renal ganglion or an inferior mesenteric ganglion. Sympathetic tone associated with kidney function can progressively decrease with aging, which may lead to renal dysfunction (e.g., decreased levels of noradrenaline production). In such instances, it may be desirable to deliver a therapy signal to an aortico-renal ganglion or an inferior mesenteric ganglion in an amount and for a time sufficient to increase sympathetic activity associated with the kidneys. This, in turn, may increase sympathetic tone in the kidneys and promote increased (or normal) renal function (e.g., increased noradrenaline levels).

Where the therapy delivery device is configured as a closed-loop system (Step 40), it will be appreciated that the method 30 can additionally or optionally include sensing a physiological parameter (discussed above) associated with ANS and/or CNS activity in the target organ. A sensor signal can then be generated based on the detected physiological parameter. Next, the therapy delivery device can be activated to adjust application of the therapy signal to the ANS and/or CNS nerve target in response to the sensor signal to treat organ aging.

In another example, the method 30 can include providing a therapy delivery device configured for percutaneous placement or implantation. For example, the therapy delivery device can comprise one or more wire or filament-shaped electrodes. Other configurations of the therapy delivery device are described above and known by those skilled in the art. The therapy delivery device can be percutaneously placed so that one or more electrodes of the therapy delivery device is/are in direct contact with a target spinal cord region. The particular target spinal cord region can be pre-determined (e.g., by a medical professional) based on the medical needs of the mammal. Non-limiting examples of CNS nerve targets, such as the spinal cord are listed in Table 1.

An introducer needle (not shown) may be employed to implant the therapy delivery device on or in the target spinal cord region. The size of the introducer needle may vary depending on the diameter of the therapy delivery device, for example. In some instances, an introducer needle may be a 12-gauge, 14-gauge, 16-gauge, 18-gauge, 20-gauge or 22-gauge needle. It should be understood that other introducer needles may be used as appropriate to the needs and skill level of the practitioner performing the surgical procedure. At least one imaging apparatus, such as a CT scan, MRI apparatus, ultrasound apparatus, fluoroscope, or the like, may be employed to monitor the surgical procedure during localization of the target spinal cord region, e.g., to assist in determining a suitable entry point for the insertion of the therapy delivery device. Once the entry point is determined, the skin overlying the entry point can be shaved and prepared with antiseptic solution. In addition to the local anesthetic, the mammal may be given intravenous sedation and prophylactic antibiotics prior to commencement of the implantation procedure.

The introducer needle can be inserted at the entry point and then advanced to the target spinal cord region. A fluoroscope, for example, may be adjusted as the introducer needle is advanced. Once the introducer needle is suitably positioned, a stylet (not shown) can be withdrawn from the introducer needle. A "test" electrode, if employed, used to test the placement of the introducer needle may then be positioned within a central channel of the needle. If a "test" electrode is not employed, the therapy delivery device that is to be employed may be positioned within the central channel of the needle. The test electrode may then be advanced to the distal tip of the introducer needle to place the test electrode on, in, or proximate the target spinal cord region.

If a "test" electrode is employed to test the placement of the introducer needle and, as such, is different from the therapy delivery device to be employed to modulate the CNS (or ANS), the "test" electrode may be removed from the introducer needle while the introducer needle is held firmly in place to prevent displacement. The therapy delivery device to be implanted may then be inserted through the central channel of the introducer needle while the introducer needle is held in place. Once the therapy delivery device to be implanted is in position, imaging and electrical stimulation may be employed to verify the correct positioning of the introducer needle and the test electrode. Alternatively, if the electrode used to test the placement of the introducer needle is the therapy delivery device to be implanted, the electrode may be left in the final test position.

Once the implanted therapy delivery device is in place, the end of the device that is outside the skin can be carefully held in place against the skin. The introducer needle may then be slowly removed, leaving the implanted therapy delivery device in place. At this point, if desired, a few small subcutaneous sutures may be placed around the therapy delivery device to hold it in the desired position. A distal end of the therapy delivery device may then be connected to an extension wire or catheter, which is tunneled to the subclavicular area, e.g., or another region that will house the energy source for the implanted therapy delivery device. The device (or devices) used to control or stimulate the therapy delivery device may be surgically implanted in the desired region by procedures known in the art.

Following implantation, the therapy delivery device can be activated. The therapy delivery device can be activated to deliver electrical energy, for example, to the target spinal cord region in an amount and for a time sufficient to effect a change in sympathetic and/or parasympathetic activity in the target organ. It will be appreciated that where the therapy delivery device is configured as a closed-loop system, the method 30 can additionally or optionally include sensing a physiological parameter (discussed above) associated with the target organ. A sensor signal can then be generated based on the detected physiological parameter. Next, the therapy delivery device can be activated to adjust application of the therapy signal to the target spinal cord region in response to the sensor signal to treat organ aging.

It will be appreciated that the present disclosure also includes methods for modulating other bodily systems to treat organ aging. In one example, the present disclosure can include modulating the immune system of a mammal to treat organ aging (e.g., a mammal affected by an autoimmune disease). One or a combination of physiological parameters associated with immune system dysfunction, which may be used to identify a mammal in need of neuromodulatory therapy, can include cytopenia, anergic response to a vaccine, abnormal levels of immune mediators (e.g., interleukins, cytokines, etc.), blood markers of immune activation (or deactivation), and other markers of autoimmune disease. Non-limiting examples of nerve targets associated with immune function can include: sympathetic chain ganglia and related pre-ganglionic and post-ganglionic nerve structures, such as a superior sympathetic chain ganglion, a middle sympathetic chain ganglion, an inferior sympathetic chain ganglion, a stellate ganglion, a thoracic sympathetic chain ganglion, a lumbosacral ganglion, and a sacral ganglion; spinal cord (e.g., cervical and thoracic segments) and dorsal root ganglia; peripheral nerves; somatic motor and sensory nerves; parasympathetic nerve structures, such as the vagal trunk; and other autonomic ganglia and plexuses, such as celiac plexus and ganglion, superior and inferior mesenteric ganglia, pulmonary plexus, phrenic ganglion, splanchnic nerves, aortico-renal ganglion, and lesser and greater splanchnic nerves. In some instance, a therapy signal can be delivered to at least one of the foregoing nerve targets in an amount and for a time sufficient to effect a change in sympathetic and/or parasympathetic activity associated with the mammal's immune system. It will further be appreciated that a closed-loop system can be used to modulate immune system function based on the level of at least one sensed physiological parameter (described above), as well as other physiological parameters, such as telomere length.

It will also be appreciated that another aspect of the present disclosure can include augmenting or increasing target organ function in a mammal. In some instances, for a mammal that is apparently healthy, it may be desirable to augment or increase function of one or more target organs to achieve an intended effect. For example, it may be desirable to effect a change in the sympathetic and/or parasympathetic nervous system to increase muscle mass in the mammal. In another example, it may be desirable to effect a change in the sympathetic and/or parasympathetic nervous system to increase nerve myelination or myelin content in the mammal. Thus, in some instances, the present disclosure can be employed to increase physical and/or mental performance (or function) in a mammal. The function of any other organ, organ system, or biological tissue that is innervated by the organ or organ system can be increased or augmented by the present disclosure.

Figure 4:
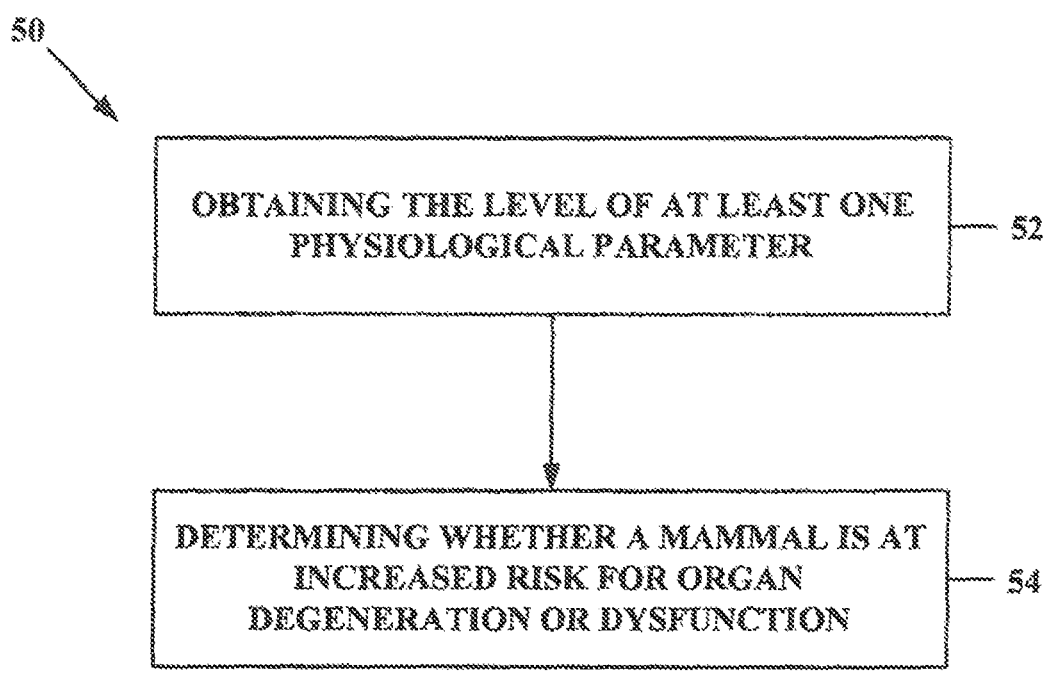
FIG. 4 is a process flow diagram illustrating a method for predicting dysfunction or degeneration in a target body organ of a mammal according to another aspect of the present disclosure.

Another aspect of the present disclosure is illustrated in FIG. 4 and includes a method 50 for predicting dysfunction or degeneration in a target body organ of a mammal. In some instances, the mammal may be suspected of having one or more dysfunctional or degenerate target body organs. In other instances, the mammal may be apparently healthy. An "apparently healthy" mammal can refer to a mammal that has not previously been diagnosed as having any signs or symptoms indicating the presence of a dysfunctional or degenerate target body organ. Apparently healthy mammals may not otherwise exhibit symptoms of a dysfunctional or degenerate target body organ. In other words, such mammals, if examined by a medical professional, would be characterized as healthy and free of symptoms of a dysfunctional or degenerate target body organ.

At Step 52, the method 50 can include obtaining one or more physiological parameters from the mammal. Physiological parameters can be obtained by, for example, blood draw, tissue biopsy, medical imaging, physical examination, etc. Next, the method 50 can include determining the level of at least one physiological parameter associated with ANS and/or CNS activity in the at least one target organ (Step 54). Methods for determining the level of the physiological parameter(s) will depend upon the particular physiological parameter(s). To determine the level of a blood- or serum-derived physiological parameter (e.g., a protein or hormone), for example, an appropriate assay (e.g., ELISA, chromatography, etc.) can be used. Biological materials can be assayed for gene expression, proteomics, and metabolomics as well. In some instances, an imaging modality (e.g., contrast-based MRI) can be used to determine the presence of certain physiological parameters, such as an organ lesion. In other instances, diagnostic instruments, such as BEG and EKG machines may be used to determine the physiological parameter(s). Similarly, assessment of aging changes can be done using approaches like telomere length on DNA from cells.

After determining the level(s) of the physiological parameter(s), the detected level(s) can be compared to a control value to determine whether the mammal has an increased risk for dysfunction or degeneration of a target body organ. In some instances, the control value can be based upon the level of a corresponding physiological parameter obtained from a control population (e.g., the general population) or a select population of mammals. In one example, the select population may be comprised of apparently healthy mammals or mammals at risk for dysfunction or degeneration of a target body organ. In other instances, the control value can be related to the value used to characterize the level of the physiological parameter(s) obtained from the mammal. For example, if the level of the physiological parameter is an absolute value, such as the units of a particular biomarker per ml of blood, the control value can also based upon the units of the particular biomarker per ml of blood in mammals of the general population or a select population. Similarly, if the level of the physiological parameter(s) is/are a representative value, such as an arbitrary unit obtained from an ELISA, the control value can also be based on the representative value.

After comparing the detected level(s) of the physiological parameter(s) with the control value(s), a determination can be made as to whether the mammal has an increased risk for dysfunction or degeneration of the target body organ. In some instances, an increased level of the detected physiological parameter(s) (as compared to the control value(s)) can be indicative of an increased risk for dysfunction or degeneration of the target body organ. In other instances, a decreased level of the detected physiological parameter(s) (as compared to the control value(s)) can be indicative of an increased risk for dysfunction or degeneration of the target body organ. Where the mammal is at an increased risk of dysfunction or degeneration in the target body organ, an appropriate therapy regimen can be selected to prevent, treat, reverse, or mitigate organ aging. In one example, organ aging can be treated according to the method 30 (FIG. 3) described above.

From the above description of the present disclosure, those skilled in the art will perceive improvements, changes and modifications. For example, other physiological parameters that may be indicative of organ dysfunction or degeneration can include presbyopia, heart rate maximum, loss of heart rate variability, and allosteric load. Such improvements, changes, and modifications are within the skill of those in the art and are intended to be covered by the appended claims. All patents, patent applications, and publication cited herein are incorporated by reference in their entirety.

The following is claimed:

1. A method for treating body organ aging in a mammal, the method comprising the steps of:
   determining the level of at least one physiological parameter associated with ANS and/or CNS activity in at least one target organ of the mammal;
   predicting dysfunction or degeneration in the at least one target body organ by comparing the determined level of the at least one physiological parameter with a control value;
   placing a therapy delivery device into electrical communication with an ANS nerve target and/or CNS nerve target associated with the at least one target organ in a mammal having an abnormal level of the at least one physiological parameter; and
   activating the therapy delivery device to deliver the therapy signal to the ANS nerve target and/or the CNS nerve target in an amount and for a time sufficient to effect a change in sympathetic and/or parasympathetic activity associated with the at least one target organ.

2. The method of claim 1, wherein the mammal is a human.

3. The method of claim 1, wherein the mammal is a domesticated animal or livestock.

4. The method of claim 1, wherein the at least one target organ is a lung and the associated ANS nerve target is a Target Nerve Structure listed in Table 1.

5. The method of claim 1, wherein the at least one target organ is a brain and the associated CNS nerve target is a Target Nerve Structure listed in Table 1.

6. The method of claim 1, wherein the at least one target organ is a heart and the associated ANS nerve target is a Target Nerve Structure listed in Table 1.

7. The method of claim 1, wherein the at least one target organ is bone marrow and the associated ANS nerve target is a Target Nerve Structure listed in Table 1.

8. The method of claim 1, wherein the at least one target organ is a muscle and the associated ANS nerve target is a Target Nerve Structure listed in Table 1.

9. The method of claim 1, wherein the at least one target organ is the skin and the associated ANS nerve target is a Target Nerve Structure listed in Table 1.

10. The method of claim 1, wherein the at least one target organ is a kidney and the associated ANS nerve target is a Target Nerve Structure listed in Table 1.

11. The method of claim 1, wherein the at least one target organ is a liver and the associated ANS nerve target is a Target Nerve Structure listed in Table 1.

12. The method of claim 1, further comprising the steps of:
   sensing a physiological parameter associated with the at least one target organ;
   generating a sensor signal based on the sensed physiological parameter; and
   activating the therapy delivery device to adjust application of the therapy signal to the ANS nerve target and/or CNS nerve target in response to the sensor signal to treat the at least one target organ.

13. The method of claim 1, wherein to effect a change in sympathetic activity comprises increasing sympathetic activity associated with the at least one target organ and wherein the dysfunction of the ANS is hyposympathetic tone or activity.

14. The method of claim 1, further including:
   identifying, before the determining step, a mammal suspected of suffering from or being afflicted by dysfunction or degeneration of at least one organ as a result of organ aging.

* * * * *